(12) United States Patent
Shah et al.

(10) Patent No.: US 6,267,951 B1
(45) Date of Patent: *Jul. 31, 2001

(54) COSMETIC COMPOSITION FOR THE NAILS AND HAIR

(75) Inventors: Arvind N. Shah, Suffern, NY (US); Ernest S. Curtis, Milford, PA (US); Harold E. Pahlck, Waldwick, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/465,473

(22) Filed: Dec. 16, 1999

Related U.S. Application Data

(63) Continuation-in-part of application No. 09/162,052, filed on Sep. 28, 1998, now Pat. No. 6,083,516, which is a continuation of application No. 08/824,510, filed on Mar. 26, 1997, now abandoned.

(51) Int. Cl.⁷ ........................................... A61K 7/04
(52) U.S. Cl. .................. 424/61; 424/70.1; 424/78.17; 424/401; 514/880
(58) Field of Search .................................. 424/401, 70.1, 424/61, 78.17; 514/880

(56) References Cited

U.S. PATENT DOCUMENTS

| | | | |
|---|---|---|---|
| 4,792,444 | 12/1988 | Fukasawa et al. | 424/63 |
| 5,030,374 | 7/1991 | Tranner | 252/90 |
| 5,143,723 | 9/1992 | Calvo et al. | 424/63 |
| 5,221,534 | 6/1993 | DesLauriers et al. | 424/78.03 |
| 5,676,935 | 10/1997 | Mellul et al. | 424/61 |
| 5,807,540 | 9/1998 | Junino et al. | 424/61 |

FOREIGN PATENT DOCUMENTS

WO 98/42298 * 10/1998 (WO).

* cited by examiner

*Primary Examiner*—Shelley A. Dodson
*Assistant Examiner*—Konata M. George
(74) *Attorney, Agent, or Firm*—Ohlandt, Greeley, Ruggiero & Perle, LLP

(57) ABSTRACT

There is provided a cosmetic composition having at least two film formers and a plasticizer in a water-in-solvent emulsion. The film formers are (1) alkyl cycloalkylacrylate copolymers having $C_{14}$ to $C_{36}$ alkyl repeating units, and (2) esters containing acids derived from rosin. The plasticizer is preferably a block copolymer. The composition is transfer and wear resistant and maintains a high shine.

30 Claims, No Drawings

COSMETIC COMPOSITION FOR THE NAILS AND HAIR

This is a continuation-in-part of U.S. patent application Ser. No. 09/162,052 that was filed on Sep. 28, 1998 and issued as U.S. Pat. No. 6,083,516 on Jul. 4, 2000, which is a continuation of U.S. Pat. No. 08/824,510 that was filed on Mar. 26, 1997 and in now abandoned.

BACKGROUND OF THE INVENTION

1. Field of the Invention

The present invention relates to cosmetic compositions. More particularly, the present invention relates to cosmetic compositions applied to the nails and hair having improved wear resistance, high shine and quick-drying time.

2. Description of the Prior Art

It is necessary that a nail lacquer not irritate the skin and nails. It is desired that nail lacquers have good application, produce a uniform film of excellent sheen, have a rapid dry time for the film, and have good adhesion to the surface of the nail. It is further desired that the nail lacquer have a certain amount of flexibility and good film strength to avoid cracking and flaking of the film.

In conventional nail enamel products, a film forming material is used with a plasticizer, which imparts good adhesion and good flexibility to the film, in a solvent (typically anhydrous). Such film forming materials include nitrocellulose alone or in association with another polymer, such as an acrylic resin or an alkyl resin. Typical solvents include butyl acetate and ethyl acetate.

Solvent-based film formers, especially nitrocellulose, are known in the art for their ability to provide a quick drying, wear resistant and shiny film. However, the product loses its high shine once the solvent has evaporated. Other limitations include an unpleasant tacky feel upon application to the nails and the environmentally unfriendly nature of solvents generally. Solvent-based cosmetic compositions include nail polishes, nail lacquers, liquid eyeliners and lipsticks.

Water-based film formers are known in the art to provide longer lasting shine because the water does not evaporate as quickly as solvents do. The additional advantages of water-based film formers as compared to solvents include being non-flammable, less damaging to nails (water causes less drying of tissue) and environmentally friendly. However, these films are slow to dry on application. Additionally, since these films remain wet for extended periods of time, compositions that have such water-based film formers adhere poorly and tend to transfer off the surface to which they are applied. This results in poor overall cosmetic wear, and requires that the user reapply the cosmetic frequently.

It would be very desirable to obtain a composition that had the wear resistance and quick drying time of a solvent-based system together with the longer lasting, high shine attributes of a water-based system. The inventors herein have discovered that it is possible to provide a water-containing system in a nail and hair composition based on the use of certain film formers, and obtain the same benefits as a nitrocellulose/solvent system.

While the copolymers of the present invention work exceptionally well in an anhydrous, solvent-based system, the benefits and results achieved in a water-containing system is particularly surprising and unexpected.

U.S. Pat. No. 5,143,723 to Calvo, et al. provides for a colored composition having pigments formed by incorporating a solvated dye into a resin. Polymeric materials approved by the Food and Drug Administration as "indirect food additives" are especially preferred resins for use in this make-up composition. These resins include styrene block polymers and ethylene-methyl acrylate copolymer resins. This patent does not provide for cosmetics with transfer resistant characteristics.

U.S. Pat. No. 5,030,374 to Tranner titled Clear Neutral Non-Foaming Rapidly-Rinseable Gel Facial Cleanser Formulation, has a block copolymer and an acrylic copolymer. This patent also does not provide for cosmetics with transfer resistant characteristics.

U.S. Pat. No. 4,792,444 to Fukasawa, et al. titled Cosmetic Comprising Fluoroalkyl (Meth)Acrylate Copolymers, has a cosmetically acceptable volatile oil and at least one copolymer. The copolymer has a first monomer selected from fluoroalkyl acrylates or fluoroalkyl methacrylates, and a second monomer selected from alkyl acrylates or methacrylates. This patent does not provide a composition that maintains its shine once the volatile oil evaporates.

U.S. Pat. No. 5,807,540 to Junino, et al. titled Nail Varnish Composition Comprising a Crosslinked Polyester, has at least one film-forming material that may have a resin, a solvent medium, and at least one crosslinked polyester. The polyester is derived from the polycondensation of adipic acid, diethylene glycol, and a polyol having at least three hydroxyl groups.

Thus, it is apparent that there is a need for compositions for the nails and hair having transfer resistant characteristics and high shine in a water-containing system.

SUMMARY OF THE INVENTION

It is an object of the present invention to provide cosmetic compositions for application to the nails and hair that maintain a high and longer-lasting shine after application.

It is another object of the present invention to provide such cosmetic compositions that have minimum transfer and improved wear characteristics.

These and other objects of the present invention are achieved by a cosmetic composition having at least two film formers and, optionally, a plasticizer in a water-containing system. The film formers are (1) alkyl cycloalkylacrylate copolymers having $C_{14}$ to $C_{36}$ alkyl repeating units, and (2) esters containing acids derived from rosin. The plasticizer is preferably a block copolymer. The composition is transfer or wear resistant, dries quickly and maintains a high and lasting shine.

DETAILED DESCRIPTION OF THE INVENTION

The present invention provides a wear-resistant cosmetic composition for the nails and hair. It has been unexpectedly discovered that, upon application, a composition having a combination of alkyl cycloalkylacrylate copolymers having $C_{14}$ to $C_{36}$ alkyl repeating units and esters containing acids derived from rosin dries quickly, has high shine and improved transfer resistance. The cosmetic composition having these film formers has a uniform application and is easy to apply. Also, the composition is flexible or non-brittle, and smooth or non-tacky. Optionally, the composition may have a mixed block copolymer as a third film former.

The first film former is one or more copolymers consisting of alkyl cycloalkylacrylate monomers. The preferred alkyl cycloalkylacrylate copolymers and the isomers thereof have the following formulas:

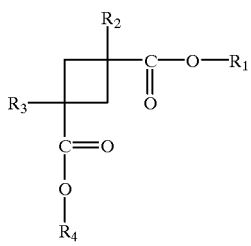

Formula A

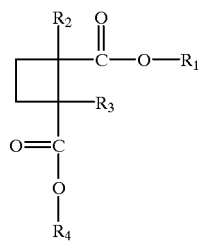

Formula B where $R_1$ to $R_4$ are each independently a hydrogen or a $C_{14}$ to $C_{36}$ alkyl group. Such alkyl cycloalkylacrylate copolymers are also known as alkyl bicycloalkylacrylate copolymers.

The preferred alkyl cycloalkylacrylate copolymers are soluble in hydrocarbons, such as isododecane, but not soluble in water. Thus, the film-forming effect of the copolymers is suitable for use in either an anhydrous system or a water-in-hydrocarbon solvent system.

Preferably, the alkyl cycloalkylacrylate copolymer is a cycloalkyl methacrylate copolymer having $C_{14}$ to $C_{36}$ alkyl repeating units. A preferred cycloalkyl methacrylate copolymer is a bicycloalkyl methacrylate copolymer manufactured by Phoenix Chemicals, Inc., Sommerville, N.J. and sold under the tradename Giovarez AC-5099 ML.

The one or more alkyl cycloalkylacrylate copolymers are preferably present in an amount from about 0.01 percent by weight (wt %) to about 75 wt % of the total weight of the composition. More preferably, the alkyl cycloalkylacrylate copolymers are about 10 wt % to about 25 wt % and, most preferably, about 15 wt % of the total weight of the composition.

The second film former is one or more esters containing acids derived from rosin. The preferred esters of the present invention are glyceryl rosinate, pentaerythrityl rosinate, silicone rosinate, and mixtures thereof. Esters of rosin acids are insoluble in water. This insolubility enhances the film-forming effect of the ester.

The esters of rosin acids are preferably present in an amount about 0.10 wt % to about 20 wt % of the total weight of the composition. More preferably, the esters of rosin acids are present in an amount about 2 wt % to about 10 wt % and, most preferably, about 5 wt % of the total weight of the composition.

The composition according to the present invention may optionally have a third film former, namely one or more block copolymers. Preferably, the block copolymers have styrene monomers, or other monomers derived from butylene, copolymerized with ethylene and propylene or butylene monomers. These block copolymers are known as styrene/ethylene/propylene tri-block copolymers and styrene/ethylene/butylene tri-block copolymers. Such tri-block copolymers may act as plasticizers as well as film formers. It should be understood that one or more of such mixed-block copolymers might be used in the present compositions. Furthermore, methods of preparing such block copolymers are well known in the art.

The preferred tri-block copolymer consists of styrene, ethylene, and propylene or butylene monomers, or the derivatives thereof, having the general structures:

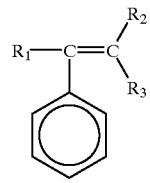

Structure A

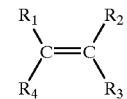

Structure B

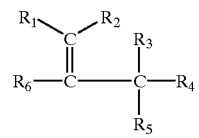

Structure C

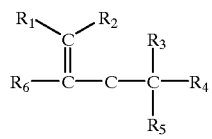

Structure D wherein $R_1$ to $R_6$ are each independently a hydrogen or a hydrophobic alkyl chain.

A preferred tri-block copolymer comprises styrene, propylene, and ethylene or butylene in a 4:2:1 ratio, with an average molecular weight of 10,000 to 20,000. This tri-block copolymer is not water-soluble. However, it is soluble in certain oils and hydrocarbon solvents, such as isoparaffin and isododecane.

A preferred styrene/ethylene/propylene tri-block copolymer is available from Brooks Industries, South Plainfield, N.J. under the tradename Gel Base I. Gel Base I comprises about 15 wt % of a styrene/ethylene/propylene tri-block copolymer dispersed in isododecane.

The one or more tri-block copolymers are present in an amount about 0.01 wt % to about 30 wt % of the total weight of the composition. More preferably, the tri-block copolymers are about 0.1 wt % to about 10 wt % and, most preferably, about 1 wt % of the total weight of the composition.

The composition preferably includes one or more volatile solvents. A volatile solvent is generally understood as a solvent with a boiling point below about 100° C. at about 1.0 atmosphere. The volatile solvents in the composition act as carriers for the other ingredients and rapidly and evenly disperse these ingredients. The one or more volatile solvents may be an emulsion having anhydrous and hydrous components. The anhydrous component in the volatile solvents will preferably include $C_6$ to $C_{20}$ hydrocarbon fractions, more preferably an isoparaffin and, most preferably, the specific $C_{12}$ fraction isododecane alone or in combination with the specific $C_{16}$ fraction isohexadecane. The anhydrous component may also include other solvents such as butyl acetate and ethyl acetate.

The one or more volatile solvents may be present in an amount about 0.01 wt % to about 80 wt % of the total weight of the composition. More preferably, the volatile solvents are present in an amount about 20 wt % to about 60 wt % and, most preferably, about 50 wt % of the total weight of the composition. However, in certain compositions, less than the maximum 80 wt % of the volatile solvents is desired due to regulations on volatile organic chemicals.

The composition may also include water in an amount up to 30 wt % of the total weight of the composition.

It is also preferred, depending on the final composition being formulated, that the composition include: a colorant such as an FD&C dye, a D&C dye, or a metal oxide; an emulsifier such as ethyl diethylene oleate or laurylmethicone copolyol; a gelling agent such as fumed silica; a chelating agent such as EDTA or sodium hexametaphosphate; a preservative such as imidazolidinyl urea; an emollient such as polyglyceryl diisostearate or diisostearyl fumarate; sodium chloride; water; fragrance; ultra-violet light screening agents; electrolytes; moisturizers; vitamins; minerals; antioxidants; biotin, and combinations thereof. The composition may also include one or more filler ingredients, such as mica, talc, cosmetic wax, cosmetic powder, pearl, and glitter coated with a polyethylene base.

A preferred composition according to the present invention has about 0.01 wt % to about 75 wt % of a cycloalkyl methacrylate copolymer; about 0.1 wt % to about 20 wt % of glyceryl rosinate, pentaerythritol rosinate, or mixtures thereof, and about 0.1 wt % to about 80 wt % volatile solvent. The preferred composition optionally has about 0.01 wt % to about 10 wt % of a block copolymer of styrene monomers, or other derivatives of butylene, copolymerized with ethylene and propylene or butylene type monomers. The preferred composition according to the present invention may also have about 0.1 wt % to about 25 wt % of at least one emulsifier, about 0.1 wt % to about 10 wt % of at least one gelling agent, about 0.1 wt % to about 15 wt % of at least one coloring agent, about 0.1 wt % to about 15 wt % of at least one filler, about 0.1 wt % to about 5 wt % of at least one electrolyte, about 0.1 wt % to about 30 wt % water, about 0.1 wt % to about 5 wt % of at least one chelating agent, about 0.1 wt % to about 5 wt % of at least one buffer, and about 0.1 wt % to about 2 wt % of at least one preservative.

The compositions of the present invention may further contain humectants, preservatives, binding agents, chelating agents, fragrances, ultraviolet light screening agents, moisturizers, vitamins, minerals, antioxidants, biotin, and combinations thereof.

The following is are examples of cosmetic compositions according to the present invention.

EXAMPLE 1

Nail Lacquer

| Ingredient | wt % |
|---|---|
| Isododecane | 38.825 |
| Demineralized water | 15.000 |
| Cycloalkyl methacrylate copolymer | 15.000 |
| Butyl acetate | 10.000 |
| Glyceryl rosinate | 5.000 |
| Polyglycerol diisostearate | 4.000 |
| Cloisonne golden bronze | 3.000 |
| Laurylmethicone copolyol | 2.000 |
| Ethyl diethylene oleate | 1.150 |
| Diisostearyl fumarate | 1.150 |
| Iron oxide coated with dimethicone/glyceryl rosinate | 1.000 |

-continued

| Ingredient | wt % |
|---|---|
| Fumed silica | 1.000 |
| Styrene/ethylene/propylene copolymers | 0.675 |
| Sodium chloride | 0.500 |
| Titanium dioxide coated with dimethicone/glyceryl rosinate | 0.500 |
| FD&C Yellow 5 Aluminum Lake coated with Barium sulfide/dimethicone/glyceryl rosinate | 0.400 |
| Sodium hexametaphosphate | 0.300 |
| Imidazolidinyl urea | 0.200 |
| Disodium EDTA | 0.200 |
| D&C Red 7 coated with dimethicone/glyceryl rosinate | 0.100 |
| | 100.000 |

EXAMPLE 2

Waterproof Lash Paint

| Ingredient | wt % |
|---|---|
| Odorless mineral spirits | 32.00 |
| Demineralized water | 15.00 |
| Isodocecane | 15.00 |
| Cosmetic powder | 13.00 |
| Cosmetic wax | 9.00 |
| Iron oxide | 5.00 |
| Pentaerythritol rosinate | 2.50 |
| Block copolymer | 2.50 |
| Alkyl cycloalkylacrylate copolymer | 2.00 |
| Hydroxylated lanolin | 1.00 |
| Propylene glycol | 1.00 |
| Glyceryl pyroglutamate monooleate | 0.50 |
| 2-phenoxyethanol | 0.50 |
| Methylparaben | 0.50 |
| Tetrasodium EDTA | 0.20 |
| Acetylated POE lanolin alcohol | 0.20 |
| Polybutene | 0.10 |
| | 100.00 |

The present invention having been described with particular reference to the preferred forms thereof, it will be obvious that various changes and modifications may be made herein without departing from the spirit and scope of the invention as defined in the appended claims.

Wherefore we claim:

1. A cosmetic composition for application to the nails and hair comprising:

an alkyl cycloalkylacrylate copolymer having $C_{14}$ to $C_{36}$ alkyl repeating units; and an ester containing acids derived from rosin.

2. The composition of claim 1, wherein said alkyl cycloalkylacrylate copolymer having $C_{14}$ to $C_{36}$ alkyl repeating units has a structure chosen from the group consisting of:

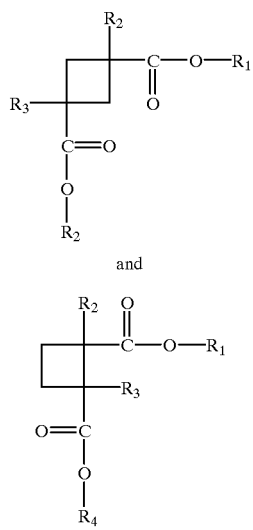

and mixtures thereof.

3. The composition of claim 1, wherein said ester of rosin acids is selected from the group consisting of glyceryl rosinate, pentaerythritol rosinate, silicone rosinate and mixtures thereof.

4. The composition of claim 1, further comprising a block copolymer.

5. The composition of claim 4, wherein said block copolymer is about 0.01 wt % to about 30 wt %, based on the total weight of the composition.

6. The composition of claim 4, wherein said block copolymer is about 0.1 wt % to about 10 wt %, based on the total weight of the composition.

7. The composition of claim 4, wherein said copolymer is a mixed-block copolymer comprised of monomers selected from the group consisting of: propylene, ethylene, butylene, styrene, derivatives thereof, and mixtures thereof.

8. The composition of claim 1, further comprising a volatile solvent.

9. The composition of claim 8, wherein said volatile solvent comprises anhydrous components derived from petroleum.

10. The composition of claim 8, wherein said volatile solvent comprises anhydrous components selected from the group consisting of isododecane, isohexadecane, butyl acetate, ethyl acetate and mixtures thereof.

11. The composition of claim 8, wherein said volatile solvent is about 0.1 wt % to about 10 wt %, based on the total weight of the composition.

12. The composition of claim 8, wherein said volatile solvent is about 20 wt % to about 60 wt %, based on the total weight of the composition.

13. The composition of claim 8, further comprising water.

14. The composition of claim 13, wherein said water is up to about 30 wt %, based on the total weight of the composition.

15. The composition of claim 1, wherein said alkyl cycloalkylacrylate copolymer is about 0.01 wt % to about 75 wt %, based on the total weight of the composition.

16. The composition of claim 1, wherein said alkyl cycloalkylacrylate copolymer is 10 wt % to 25 wt %, based on the total weight of the composition.

17. The composition of claim 1, wherein said ester of rosin acids is about 0.10 wt % to about 20 wt %, based on the total weight of the composition.

18. The composition of claim 1, wherein said ester of rosin acids is about 2 wt % to about 10 wt %, based on the total weight of the composition.

19. A method of improving transfer/wear resistance and/or shine of a cosmetic composition comprising:

combining into said cosmetic composition, based on the total weight of the composition:
about 0.01 wt % to about 75 wt % of an alkyl cycloalkylacrylate copolymer having $C_{14}$ to $C_{36}$ alkyl repeating units; and
about 0.1 wt % to about 20 wt % of one or more esters containing acids derived from rosin; and
applying said cosmetic composition onto the nails or hair of a person.

20. The method of claim 19, wherein the composition further comprises about 0.01 wt % to about 80 wt % of a volatile solvent, based on the total weight of the composition.

21. The method of claim 19, wherein the composition further comprises about 0.01 wt % to about 30 wt % of a block copolymer, based on the total weight of the composition.

22. The method of claim 21, wherein said block copolymer is a mixed-block copolymer comprised of monomers selected from the group consisting of: propylene, ethylene, thereof, styrene, derivatives of butylene, and mixtures thereof.

23. The method of claim 19, wherein the composition further comprises up to about 30 wt % water, based on the total weight of the composition.

24. The composition of claim 1, wherein said ester of rosin acids is selected from the group consisting of glyceryl rosinate, pentaerythritol rosinate, silicone rosinate, and mixtures thereof.

25. The composition of claim 1, wherein said ester of rosin acids includes a silicone rosinate.

26. The method of claim 19, wherein said ester of rosin acids includes a silicone rosinate.

27. A method of enhancing and/or improving the shine provided by a nail and/or hair cosmetic composition comprising:

adding an ester of rosin acids to said nail and/or hair composition.

28. The method of claim 27, wherein said ester is about 0.10 wt % to about 20 wt % based on the total weight of the composition.

29. The method of claim 27, wherein said ester is selected from the group consisting of glyceryl rosinate, pentaerythritol rosinate, silicone rosinate, and mixtures thereof.

30. The method of claim 27, wherein said ester includes a silicone rosinate.

* * * * *

UNITED STATES PATENT AND TRADEMARK OFFICE
CERTIFICATE OF CORRECTION

PATENT NO. : 6,267,951 B1
DATED : July 31, 2001
INVENTOR(S) : Arvind N. Shah, Ernest S. Curtis and Harold E. Pahlck It is certified that error appears in the above-identified patent and that said Letters Patent is hereby corrected as shown below:

Column 8,
Line 4, delete "thereof" and insert -- butylene -- and delete "of butylene" and insert -- thereof --;

Signed and Sealed this

Thirtieth Day of April, 2002

Attest:

Attesting Officer

JAMES E. ROGAN
Director of the United States Patent and Trademark Office